(12) United States Patent
Bartos

(10) Patent No.: US 9,260,370 B2
(45) Date of Patent: Feb. 16, 2016

(54) PROCESS FOR USING DEHYDRATION TOWER CONDENSATE AS A PURIFICATION MAKEUP SOLVENT

(71) Applicant: BP Corporation North America Inc., Naperville, IL (US)

(72) Inventor: Thomas M. Bartos, Naperville, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/585,520

(22) Filed: Dec. 30, 2014

(65) Prior Publication Data

US 2015/0183713 A1 Jul. 2, 2015

Related U.S. Application Data

(60) Provisional application No. 61/921,799, filed on Dec. 30, 2013.

(51) Int. Cl.
| | |
|---|---|
| *C07C 51/16* | (2006.01) |
| *C07C 51/487* | (2006.01) |
| *C07C 51/265* | (2006.01) |
| *C07C 51/42* | (2006.01) |

(52) U.S. Cl.
CPC ............. *C07C 51/487* (2013.01); *C07C 51/265* (2013.01); *C07C 51/42* (2013.01)

(58) Field of Classification Search
None
See application file for complete search history.

(56) References Cited

U.S. PATENT DOCUMENTS

| | | |
|---|---|---|
| 5,723,656 A | 3/1998 | Abrams |
| 6,137,001 A | 10/2000 | Broeker et al. |
| 7,935,844 B2 | 5/2011 | Bartos |
| 7,935,845 B2 | 5/2011 | Bartos et al. |
| 8,173,834 B2 | 5/2012 | Bartos |
| 8,779,185 B2 * | 7/2014 | Bartos .......................... 562/412 |
| 2012/0220800 A1 | 8/2012 | Bartos |

FOREIGN PATENT DOCUMENTS

WO  WO-03/091195  11/2003

* cited by examiner

*Primary Examiner* — Yevegeny Valenrod
(74) *Attorney, Agent, or Firm* — Robert N. Carpenter

(57) ABSTRACT

Processes for manufacturing purified aromatic carboxylic acids include: oxidizing a substituted aromatic compound in a reaction zone to form a crude aromatic carboxylic add; transferring a vapor phase from the reaction zone to a separation zone, the vapor phase containing water and a plurality of organic compounds including at least one oxidation byproduct; withdrawing an organic-depleted water stream from the separation zone and combining at least a portion of the organic-depleted water stream with at least a portion of the crude aromatic carboxylic acid in a purification zone; and purifying the crude aromatic carboxylic acid in the purification zone.

19 Claims, 2 Drawing Sheets

PROCESS FOR USING DEHYDRATION TOWER CONDENSATE AS A PURIFICATION MAKEUP SOLVENT

CROSS-REFERENCE TO RELATED APPLICATIONS

This application claims benefit of U.S. provisional patent application Ser. No. 61/921,799 filed Dec. 30, 2013.

TECHNICAL FIELD

The present teachings relate generally to processes for manufacturing purified aromatic carboxylic acids, and in particular, to utilizing dehydration tower condensate as make-up water in a purification reaction.

BACKGROUND

Terephthalic acid (TA) and other aromatic carboxylic acids may be used in the manufacture of polyesters (e.g., via their reaction with ethylene glycol and/or higher alkylene glycols). Polyesters in turn may be used to make fibers, films, containers, bottles, other packaging materials, molded articles, and the like.

In commercial practice, aromatic carboxylic acids have been made by liquid phase oxidation of methyl-substituted benzene and naphthalene feedstocks in an aqueous acetic acid solvent. The positions of the methyl substituents correspond to the positions of carboxyl groups in the aromatic carboxylic acid product. Air or other sources of oxygen (e.g., typically in a gaseous state) have been used as oxidants in the presence, for example, of a bromine-promoted catalyst that contains cobalt and manganese. The oxidation is exothermic and yields aromatic carboxylic acid together with by-products, including partial or intermediate oxidation products of the aromatic feedstock, and acetic acid reaction products (e.g., methanol, methyl acetate, and methyl bromide). Water is also generated as a by-product.

Pure forms of aromatic carboxylic acids are oftentimes desirable for the manufacture of polyesters to be used in important applications (e.g., fibers and bottles). Impurities in the acids (e.g., by-products generated from oxidation of aromatic feedstocks and, more generally, various carbonyl-substituted aromatic species) are thought to cause and/or correlate with color formation in polyesters made therefrom, which in turn leads to off-color in polyester converted products. Aromatic carboxylic acids having reduced levels of impurities may be made by further oxidizing crude products from liquid phase oxidation as described above at one or more progressively lower temperatures and oxygen levels. In addition, partial oxidation products may be recovered during crystallization and converted into the desired acid product.

Pure forms of terephthalic acid and other aromatic carboxylic acids having reduced amounts of impurities—for example, purified terephthalic acid (PTA)—have been made by catalytically hydrogenating less pure forms of the acids or so-called medium purity products in solution at elevated temperature and pressure using a noble metal catalyst. Less pure forms of the acids may include crude product that contains aromatic carboxylic acid and by-products from liquid phase oxidation of the aromatic feedstock. In commercial practice, liquid phase oxidation of alkyl aromatic feed materials to crude aromatic carboxylic acid, and purification of the crude product, are oftentimes conducted in continuous integrated processes in which crude product from the liquid phase oxidation is used as a starting material for the purification.

In one conventional integrated process for manufacturing pure forms of aromatic carboxylic acids via liquid phase oxidation of aromatic hydrocarbon feed materials, a dehydration tower operated at ambient pressure produces an overhead water vapor phase that is subsequently condensed, and a portion of the resulting condensate is used as reflux to the dehydration tower. The condensate typically contains one or a plurality of organic compounds, and therefore the portion of the condensate that is not refluxed to the dehydration tower may be unsuitable for use in other parts of the process, such as in makeup water in a purification process, unless the condensate stream first undergoes additional treatment to remove organic impurities. The additional treatments add both capital and variable costs to the overall process economics.

There remains a need to reduce the costs of processes for the manufacturing purified aromatic carboxylic acids.

SUMMARY

The scope of the present invention is defined solely by the appended claims, and is not affected to any degree by the statements within this summary.

By way of introduction, in some embodiments, the present teachings are directed to facilitating the manufacture of aromatic carboxylic acids by liquid phase oxidation of aromatic hydrocarbon feed materials with improved waste water treatment loading and/or reduced requirements for using treated water as purification makeup solvent.

In integrated processes for manufacturing pure forms of aromatic carboxylic acids via liquid phase oxidation of aromatic hydrocarbon feed materials and subsequent purification of the crude product (e.g., by hydrogenation of a solution of the crude product in a liquid comprising water), a water stream taken as a side draw from a dehydration tower is organic-depleted and may be suitable for use as purification solvent makeup elsewhere in the process.

A process for manufacturing a purified aromatic carboxylic acid in accordance with the present teachings includes: oxidizing a substituted aromatic compound in a reaction zone to form a crude aromatic carboxylic acid; transferring a vapor phase from the reaction zone to a separation zone, the vapor phase containing water and a plurality of organic compounds; withdrawing a high pressure gas containing water vapor removed from the separation zone and transferring the high pressure gas to a condensing zone; withdrawing an organic-depleted water stream from the separation zone and combining at least a portion of the organic-depleted water stream with at least a portion of the crude aromatic carboxylic acid in a purification zone; purifying the crude aromatic carboxylic acid in the purification zone; separating a purification mother liquor from a solid purified aromatic carboxylic acid in the purification zone; and removing organic compounds from the purification mother liquor.

A process for manufacturing purified terephthalic acid in accordance with the present teachings includes: oxidizing para-xylene in a reaction zone to form crude terephthalic acid, wherein the oxidizing includes contacting the para-xylene with gaseous oxygen in a liquid phase oxidation reaction mixture that includes acetic acid, water, and a bromine-promoted catalyst composition; transferring a vapor phase from the reaction zone to a separation zone, the vapor phase containing water, methanol, methyl acetate, and acetic acid; withdrawing a high pressure gas containing water vapor removed from the separation zone and transferring the high pressure gas to a condensing zone; withdrawing an organic-depleted water stream from the separation zone and combining at least a portion of the organic-depleted water stream with at least a portion of the crude terephthalic acid in a purification zone, wherein an amount of methyl acetate and/or methanol in the organic-depleted water stream is less than a corresponding amount in the vapor phase; purifying the crude aromatic carboxylic acid in the purification zone; separating a purification mother liquor from a solid purified terephthalic acid in the purification zone; and removing organic compounds from the purification mother liquor.

DETAILED DESCRIPTION

Figure 1:
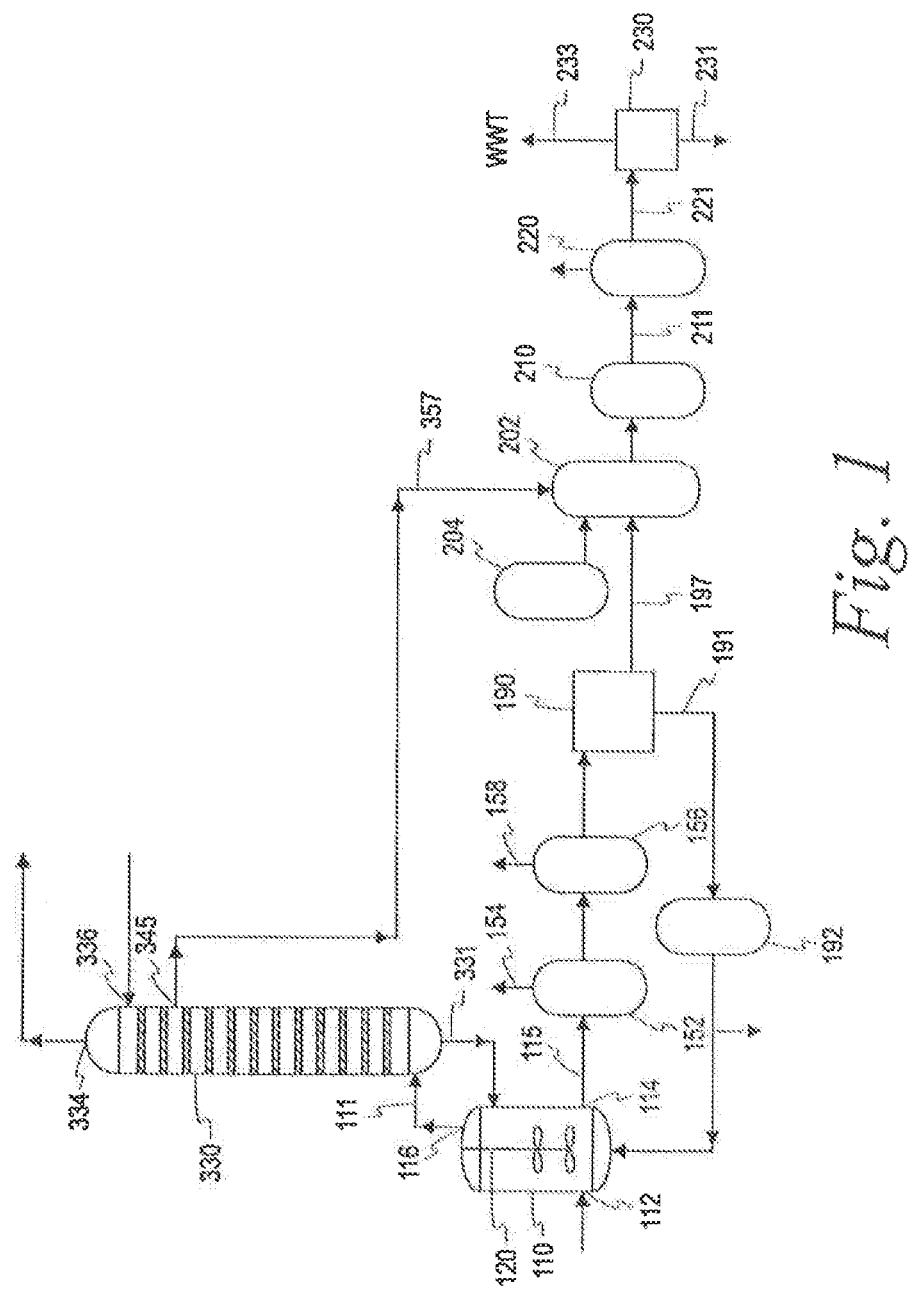
FIG. 1 shows a process flow diagram for manufacturing purified forms of aromatic carboxylic acids in accordance with the present teachings.

By way of general introduction, a process for manufacturing a purified aromatic carboxylic acid in accordance with the present teachings comprises: oxidizing a substituted aromatic compound in a reaction zone to form a crude aromatic carboxylic acid; transferring a vapor phase from the reaction zone to a separation zone, the vapor phase comprising water and a plurality of organic compounds including at least one oxidation by-product; withdrawing an organic-depleted water stream from the separation zone, the organic-depleted water stream being substantially free of the at least one oxidation by-product, and combining at least a portion of the organic-depleted water stream with at least a portion of the crude aromatic carboxylic acid in a purification zone; purifying the crude aromatic carboxylic acid in the purification zone; separating a purification mother liquor from a solid purified aromatic carboxylic acid in the purification zone; and removing organic compounds from the purification mother liquor.

In some embodiments, the oxidizing comprises contacting the substituted aromatic compound with gaseous oxygen in a liquid phase oxidation reaction mixture comprising a monocarboxylic acid solvent, water, and a catalyst composition. In some embodiments, the organic-depleted water stream comprises water and, in some embodiments, further comprises at least a portion of the monocarboxylic acid solvent. In some embodiments, the monocarboxylic acid solvent comprises acetic acid.

In some embodiments, the plurality of organic compounds in the vapor phase comprises an alkyl ester (e.g., methyl acetate, ethyl acetate, etc.), an alcohol (e.g., methanol, ethanol, etc.), unreacted and/or partially reacted substituted aromatic compounds (e.g., para-xylene, etc.), or the like, and combinations thereof. In some embodiments, a process for manufacturing a purified aromatic carboxylic acid in accordance with the present teachings further comprises reducing an amount of one or more organic compounds in the organic-depleted water stream relative to a corresponding amount in the vapor phase. In some embodiments, the organic compounds are selected from the group consisting of methyl acetate, methanol, para-xylene, and combinations thereof.

In some embodiments, a separation zone in accordance with the present teachings comprises a dehydration tower. In some embodiments, the separation zone comprises a plurality of dehydration towers. In some embodiments, the separation zone comprises a first dehydration tower and a second dehydration tower in fluid communication with the first dehydration tower.

A separation device in accordance with the present teachings may include a side draw configured for egress of the organic-depleted water stream. By way of example, the above-described second dehydration tower configured to operate above ambient pressure may include a side draw from which water substantially depleted of organic compounds such as alcohols, alkyl esters, and/or substituted aromatic compounds may be removed. In some embodiments, an amount of an alkyl ester, an alcohol, or a combination thereof in the organic-depleted water stream is less than a corresponding amount in the vapor phase. In some embodiments, the alkyl ester comprises methyl acetate and/or the alcohol comprises methanol.

In some embodiments, the vapor phase transferred from the reaction zone to the separation zone comprises solvent monocarboxylic acid which, in some embodiments, comprises acetic acid. In some embodiments, the vapor phase further comprises methyl acetate, methanol, and/or para xylene. In some embodiments, the vapor phase comprises methyl acetate, and an amount of the methyl acetate in the organic-depleted water stream is less than a corresponding amount in the vapor phase. In some embodiments, the vapor phase comprises methanol, and an amount of the methanol in the organic-depleted water stream is less than a corresponding amount in the vapor phase. In some embodiments, the vapor phase comprises methyl acetate, methanol, and para-xylene, and the amounts of the methyl acetate, methanol, and para-xylene in the organic-depleted water stream are less than the corresponding amounts in the vapor phase. In some embodiments, the first dehydration tower is configured to operate at ambient pressure, and the second dehydration tower is configured to operate above ambient pressure.

In some embodiments, a purification zone in accordance with the present teachings comprises a hydrogenation reactor. In some embodiments, the purifying comprises contacting an aqueous solution that comprises at least a portion of the crude aromatic carboxylic acid and at least a portion of the organic-depleted water stream with hydrogen in the presence of a catalyst.

In some embodiments, the purification mother liquor separated from the solid purified aromatic carboxylic acid in the purification zone is not recycled back to the separation zone. In some embodiments, one or a plurality of organic compounds is removed from the purification mother liquor outside of the separation zone. In some embodiments, all or at least a portion of the purification mother liquor is sent to waste water treatment.

A process for manufacturing purified terephthalic acid in accordance with the present teachings comprises: oxidizing para-xylene in a reaction zone to form crude terephthalic acid, wherein the oxidizing comprises contacting the para-xylene with gaseous oxygen in a liquid phase oxidation reaction mixture that comprises acetic acid, water, and a bromine-promoted catalyst composition; transferring a vapor phase from the reaction zone to a separation zone, the vapor phase comprising water, methanol, methyl acetate, and acetic acid; withdrawing a high pressure gas comprising water vapor removed from the separation zone and transferring the high pressure gas to a condensing zone; withdrawing an organic-depleted water stream from the separation zone and combining at least a portion of the organic-depleted water stream with at least a portion of the crude terephthalic acid in a purification zone, wherein an amount of methyl acetate and/or methanol in the organic-depleted water stream is less than a corresponding amount in the vapor phase; purifying the crude aromatic carboxylic acid in the purification zone; separating a purification mother liquor from a solid purified terephthalic acid in the purification zone; and removing organic compounds from the purification mother liquor.

Additional features of the above-described processes for manufacturing purified forms of aromatic carboxylic acid in accordance with the present teachings will now be described in reference to the drawing figures.

FIG. 1 shows a process flow diagram for manufacturing purified forms of aromatic carboxylic acids in accordance with the present invention. As shown in FIG. 1, the apparatus includes: an oxidation reactor 110 configured for liquid phase oxidation of feedstock; a separation zone configured for producing an organic-depleted water stream, and comprising one or a plurality of separation devices, such as column 330; a crystallization zone configured for forming crude solid product from the liquid phase oxidation reaction mixture, and comprising crystallization vessels 152 and 156; a solid-liquid separation device 190 configured for separating crude solid product (and oxidation by-products) from liquid; a purification solution makeup vessel 202 configured for preparing slurries and/or solutions of crude solid product in purification reaction solvent, such as the organic-depleted water stream from column 330; a crystallization vessel 220 configured for forming purified solid product from the purification solution; and a solid-liquid separation device 230 configured for separating purified solid product from liquid. The integration of processes in FIG. 1 is meant to be purely representative, and various other integrated, and non-integrated configurations may likewise be used.

Liquid and gaseous streams and materials used in the process represented in FIG. 1 may be directed and transferred through suitable transfer lines, conduits, and piping constructed, for example, from materials appropriate for process use and safety. It will be understood that particular elements may be physically juxtaposed and, where appropriate, may have flexible regions, rigid regions, or a combination of both. In directing streams or compounds, intervening apparatuses and/or optional treatments may be included. By way of example, pumps, valves, manifolds, gas and liquid flow meters and distributors, sampling and sensing devices, and other equipment (e.g., for monitoring, controlling, adjusting, and/or diverting pressures, flows and other operating parameters) may be present.

Representative aromatic feedstock materials suitable for use in the oxidation reactor 110 include aromatic compounds, such as aromatic hydrocarbons substituted at one or more positions with at least one group that is oxidizable to a carboxylic acid group. In some embodiments, the positions of the substituents correspond to the positions of the carboxylic acid groups of the aromatic carboxylic acid being prepared. In some embodiments, the oxidizable substituents include alkyl groups (e.g., methyl, ethyl, and/or isopropyl groups). In other embodiments, the oxidizable substituents include oxygen-containing groups, such as a hydroxyalkyl, formyl, aldehyde, and/or keto groups. The substituents may be the same or different. The aromatic portion of feedstock compounds may be a benzene nucleus or it may be bi- or polycyclic (e.g., a naphthalene and/or anthracene nucleus). In some embodiments, the number of oxidizable substituents on the aromatic portion of the feedstock compound is equal to the number of sites available on the aromatic portion. In other embodiments, the number of oxidizable substituents on the aromatic portion of the feedstock is fewer than all such sites (e.g., in some embodiments 1 to 4 and, in some embodiments, 2). Representative feed compounds that may be used in accordance with the present teachings—alone or in combinations—include but are not limited to toluene; ethylbenzene and other alkyl-substituted benzenes; o-xylene; p-xylene; m-xylene; tolualdehydes, toluic acids, alkyl benzyl alcohols, 1-formyl-4-methylbenzene, 1-hydroxymethyl-4-methylbenzene; methylacetophenone; 1,2,4-trimethylbenzene; 1-formyl-2,4-dimethyl-benzene; 1,2,4,5-tetramethyl-benzene; alkyl-, formyl-, acyl-, and hydroxylmethyl-substituted naphthalenes (e.g., 2,6-dimethylnaphthalene, 2,6-diethylnaphthalene, 2,7-dimethylnaphthalene, 2,7-diethylnaphthalene, 2-formyl-6-methylnaphthalene, 2-acyl-6-methylnaphthalene, 2-methyl-6-ethylnaphthalene, and the like); and the like; and partially oxidized derivatives of any of the foregoing; and combinations thereof. In some embodiments, the substituted aromatic compound comprises a methyl-, ethyl-, and/or isopropyl-substituted aromatic hydrocarbon. In some embodiments, the substituted aromatic compound comprises an alkyl-substituted benzene, o-xylene, p-xylene, m-xylene, or the like, or combinations thereof.

Aromatic carboxylic acids manufactured in accordance with the present teachings include mono- and polycarboxylated species having one or more aromatic rings. In some embodiments, the aromatic carboxylic acids are manufactured by reaction of gaseous and liquid reactants in a liquid phase system. In some embodiments, the aromatic carboxylic acid comprises only one aromatic ring. In other embodiments, the aromatic carboxylic acid comprises a plurality (e.g., two or more) aromatic rings that, in some embodiments, are fused (e.g., naphthalene, anthracene, etc.) and, in other embodiments, are not. In some embodiments, the aromatic carboxylic acid comprises only one carboxylic acid (e.g., —$CO_2H$) moiety or a salt thereof (e.g., —$CO_2X$, where X is a cationic species including but not limited to metal cations, ammonium ions, and the like). In other embodiments, the aromatic carboxylic acid comprises a plurality (e.g., two or more) of carboxylic acid moieties or salts thereof. Representative aromatic carboxylic acids include terephthalic acid, trimesic acid, trimellitic acid, phthalic acid, isophthalic acid, benzoic acid, naphthalene dicarboxylic acids, and the like, and combinations thereof. In one embodiment, the present teachings are directed to manufacture of pure forms of terephthalic acid including purified terephthalic acid (PTA) and so-called medium purity terephthalic acids.

A representative type of oxidation that may be conducted in the oxidation reactor 110 is a liquid phase oxidation that comprises contacting oxygen gas and a feed material comprising an aromatic hydrocarbon having substituents oxidizable to carboxylic acid groups in a liquid phase reaction mixture. In some embodiments, the liquid phase reaction mixture comprises a monocarboxylic acid solvent and water in the presence of a catalyst composition comprising at least one heavy metal component (e.g., Co, Mn, V, Mo, Cr, Fe, Ni, Zi, Ce, Hf, or the like, and combinations thereof) and a promoter (e.g., halogen compounds, etc.). In some embodiments, the oxidation is conducted at elevated temperature and pressure effective to maintain a liquid phase reaction mixture and form a high temperature, high-pressure vapor phase. In some embodiments, oxidation of the aromatic feed material in the liquid phase oxidation produces aromatic carboxylic acid as well as reaction by-products, such as partial or intermediate oxidation products of the aromatic feed material and/or solvent by-products. In some embodiments, the aromatic carboxylic acid comprises terephthalic acid, and the oxidizing comprises contacting para-xylene with gaseous oxygen in a liquid phase oxidation reaction mixture that comprises acetic acid, water, and a bromine-promoted catalyst composition. The liquid-phase oxidation and associated processes may be conducted as a batch process, a continuous process, or a semi-continuous process. The oxidation may be conducted in one or more reactors.

In a representative embodiment, such as may be implemented as shown in AG. 1, liquid feed material comprising at least about 99 wt. % of a substituted aromatic hydrocarbon, aqueous acetic acid solution (e.g., containing about 70 to about 95 wt. % acetic acid), soluble compounds of cobalt and manganese (e.g., such as their respective acetates) as sources of catalyst metals, bromine (e.g., hydrogen bromide) as catalyst promoter, and air may be continuously charged to oxidation reaction vessel 110 through inlets, such as inlet 112. In some embodiments, vessel 110 is a pressure-rated, continuous-stirred tank reactor.

In some embodiments, stirring may be provided by rotation of an agitator 120, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

The substituted aromatic hydrocarbon is oxidized in reactor 110, predominantly to aromatic carboxylic acid by-products. Oxidation by-products may also be formed, including partial and intermediate oxidation products. In the one embodiment where the substituted aromatic hydrocarbon is para-xylene, for example, by-products that may form in addition to terephthalic acid 4-carboxybenzaldehyde, 1,4-hydroxymethyl benzoic acid, p-toluic acid, benzoic acid.

Since the oxidation reaction is exothermic, heat generated by the reaction may cause boiling of the liquid phase reaction mixture and formation of an overhead vapor phase that comprises vaporized acetic acid, water vapor, gaseous by-products from the oxidation reaction, carbon oxides, nitrogen from the air charged to the reaction, unreacted oxygen, and the like, and combinations thereof. The overhead vapor may be removed from the reactor through vent 116 and sent in a stream 111 to a separation zone (e.g., a high-pressure distillation column 330) for further processing as further described below in reference to FIG. 2. An exit gas withdrawn from the column 330 at vent 334 may be directed to a condensing zone as further described, for example, in U.S. Pat. Nos. 5,723,656, 6,137,001, 7,935,844, 7,935,845, and 8,173,834.

The separation device 330 is configured and operated for separating $C_{1-8}$ monocarboxylic acid and water in the high-pressure and temperature oxidation reactor overhead gas introduced to the device. In addition, separation device 330 is configured for apportioning by-products of the liquid phase oxidation, such that a first liquid phase rich in the monocarboxylic acid, a second liquid phase rich in water but organic-depleted and substantially free of the solvent and/or its by-products, and a second high-pressure vapor phase comprising water and substantially free of solvent and by-products of the aromatic feed are formed. In some embodiments, direct association or close coupling of the oxidation reactor and separation device are effectuated by direct connection or by suitable pressure-rated piping or other conduits between one or more vents in the oxidation reaction vessel and one or more gas inlets to the separation device. In some embodiments, a vapor phase under liquid phase reaction conditions is removed from the reaction vessel and introduced into the separation device at the same or substantially the same temperature and pressure as in the reaction zone.

At least a portion of the organic-depleted water phase is withdrawn from the separation device 330 at a side draw 345. In this manner, the separation device 330 acts as a stripper for removing organic compounds from the water phase and therefore the resulting organic-depleted water stream is suitable for use in other parts of the process. For example, the organic-depleted water stream may be suitable for use as purification solvent make-up in vessel 202, as described below. In some embodiments, the organic-depleted water stream is suitable for use a purification make-up solvent without further treatment to remove organic impurities. The use of organic-depleted water from the separation zone as purification solvent makeup, avoids the expense of desalination equipment that might otherwise be needed to produce the demineralized water for the purification zone. The use of the organic-depleted water stream in the purification zone avoids the necessity of sending the organic-depleted water stream to waste water treatment.

The separation device 330 is configured and operated such that the organic-depleted water withdrawn through sidedraw 345 is substantially free of oxidation by-products of the reaction feedstock. In some embodiments, the organic-depleted stream contains less than 1 ppmw of oxidation by-products, or less than 100 ppbw of oxidation by-products, or less than 10 ppbw oxidation by-products.

The separation device 330 is also configured and operated such that the organic-depleted water withdrawn through sidedraw 345 is substantially free of oxidation by-products of the solvent. In some embodiments, the organic-depleted water stream contains less than 0.05 wt % alcohol, or less than 0.03 wt % alcohol, or less than 0.02 wt % alcohol. In some embodiments, the organic-depleted water stream contains less than 0.05 wt % alkyl ester, or less than 0.03 wt % alkyl ester, or less than 0.02 wt % alkyl ester.

For example, in embodiments where paraxylene is oxidized to terephthalic acid, the organic-depleted water stream contains less than 1 ppmw of paratoluic acid, or less than 100 ppbw of paratoluic acid, or less than 10 ppbw paratoluic acid. In some embodiments, the organic-depleted water stream contains less than 0.05 wt % methanol, or less than 0.03 wt % methanol, or less than 0.02 wt % methanol. In some embodiments, the organic-depleted water stream contains less than 0.05 wt % methyl acetate, or less than 0.03 wt % methyl acetate, or less than 0.02 wt % methyl acetate.

Figure 2:
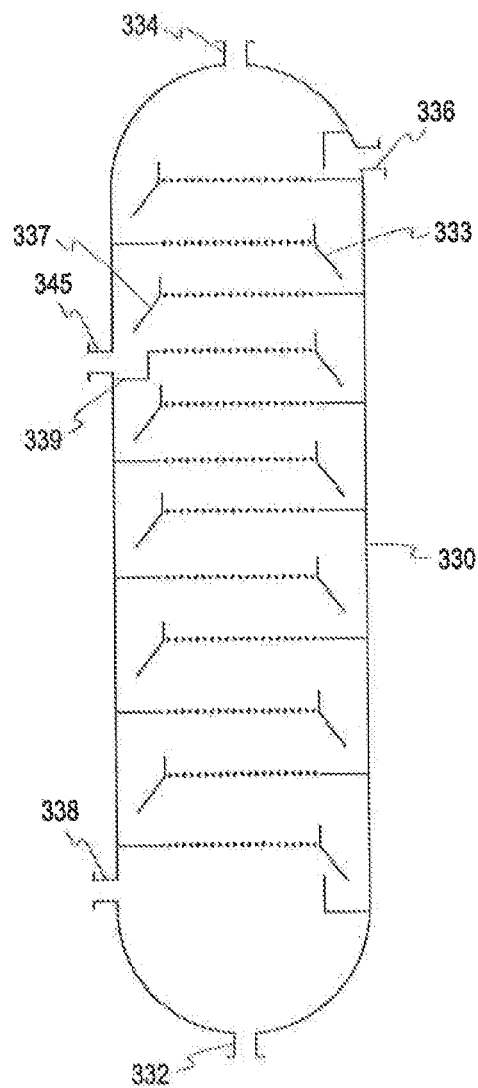
FIG. 2 shows a cross-sectional view of the separation device 330 shown in FIG. 1.

FIG. 2 shows a representative implementation of the separation device 330 of FIG. 1. In some embodiments, as shown in FIG. 2, the separation device 330 comprises a high pressure distillation. The separation device 330 is configured and operated to receive a high-pressure vapor phase removed from oxidation reactor 110 in stream 111, and for removal of a second high-pressure vapor phase through gas outlet 334. The high-pressure vapor phase may be transferred from the reaction zone of a liquid phase oxidation to the separation zone directly (e.g., by mounting a separation device directly or in close association with an oxidation reaction vessel or other part of the reaction zone) or indirectly (e.g., via suitable conduits, valves, pumps, and/or the like) for effecting transfer.

The separation device 330 also includes an inlet 336 for the introduction of reflux liquids, for an example, condensate formed in an overhead condenser (not shown). The side draw outlet 345 is positioned for removal of an organic-depleted water phase from the column. The structure in the interior space of the column and the positioning between an inlet for receiving high-pressure vapor phase from oxidation reactor 110 and reflux inlet 336 provides a fractionating zone in the interior. In some embodiments, the reflux liquid supplied to the separation device 330 at inlet 336 comprises water. Any suitable source of liquid comprising water that is substantially free of impurities detrimental to the separation or other parts of the integrated process may be utilized. In some embodiments, demineralized water or other purified water sources may be used. In some embodiments, the reflux liquid comprises a liquid condensed from a high-pressure gas removed from a separation zone and/or condensing zone in accordance with the present teachings.

In some embodiments, the reflux liquid is free or substantially free of oxidation reaction by-products, and in some embodiments, is free or substantially free of oxidation reaction by-products of the substituted aromatic compound feedstock. Accordingly, in some embodiments, the reflux liquid does not include reflux from streams containing oxidation by-products. In one embodiment, the reflux does not contain purification mother liquor as more fully described below.

In some embodiments, as shown in FIG. 2, the column 330 comprises at least one lower outlet 332 configured for removing liquid from the column, for example, to oxidation reaction vessel 110. In some embodiments, gas inlet 338 is positioned at a lower portion of the column and is configured to receive oxidation reactor off-gas. In some embodiments, vent 334 is located at an upper portion of column 330 and is configured for removing a second high-pressure vapor phase as an exit gas. As shown in FIG. 2, the interior region of column 330 includes a plurality of trays, such as 333 and 337, which are configured to provide theoretical equilibrium stages for separating, for example, organic compounds (e.g., methanol, methyl acetate, paraxylene, and/or the like) from water in a high pressure vapor phase removed from the liquid phase oxidation reaction vessel 110. In some embodiments, a tray configured with a boot, trough, accumulation channel, and/or other collection means 339 at a circumferential boundary thereof is in flow communication with side draw outlet 345 and configured for collecting organic-depleted water for eventual removal through side draw outlet 345.

A fractionating zone of the separation device is configured with a plurality of theoretical equilibrium stages, such as may be provided by internal trays, structured packing, combinations of trays and packing, or other structure or combinations thereof that provide surfaces within the interior of the device for mass transfer between gaseous and liquid phases.

In some embodiments, a separation device with structured packing has at least about 3 beds or zones of packing and, in some embodiments, about 4 to about 8 such beds, to provide adequate surface and theoretical equilibrium stages for separation. An example of a suitable packing material is FLEXIPAC structured packing, which is available from KGGP LLC in the form of thin sheets of corrugated metal arranged in a crisscrossing relationship that creates flow channels, such that the intersections create mixing points for liquid and vapor phases. In some embodiments, a separation device with trays includes about 30 to about 90 trays, at least about 70% of which are positioned between the inlet 338 for the high-pressure gas introduced to the separation device from the reaction vessel and at least one reflux liquid inlet 336. In some embodiments, the trays are in the form of sieve or bubble cap trays having separation efficiencies of about 30 to about 60%. The number of trays for a given number of theoretical equilibrium stages may be calculated by dividing the number of stages by the efficiency of the trays.

During use, the gas and liquid phases in the separation device 330 may be at elevated temperatures and include water, solvent monocarboxylic acid, and other corrosive components (e.g., bromine compounds and disassociation products thereof, such as hydrogen bromide, that may be present in the overhead gas of the oxidation reaction when the catalyst includes a bromine source). Thus, in some embodiments, the internal structure and other features of the separation device 330 configured to contact gases and liquids during operation may be constructed of metals that are resistant to corrosion and other damage. In some embodiments, titanium metal is used for the construction of surfaces such as the trays, packings, and/or other structures in the fractionating zone. The titanium surfaces may be subject to undesirable accumulation of solid deposits comprising iron oxides from impurities present in the liquids circulated through the equipment. Representative separation devices for use in accordance with the present teachings include various columns or towers designed for providing contact between gas and liquid phases flowing therethrough for mass transfer between the phases in a plurality of theoretical equilibrium stages (a.k.a, theoretical plates) that are configured for separating and preferentially apportioning components of the flowing gas and liquid phases.

In some embodiments, contact between flowing gas and liquid phases may be promoted by internal structure, such as trays or packing, which provides surfaces for gas-liquid contact and theoretical equilibrium stages for separations. In some embodiments, the temperature of the high-pressure vapor phase removed from a liquid phase oxidation is sufficiently high that no reboiling capability is needed beyond that provided by the liquid phase oxidation reaction. In some embodiments, a countercurrent flow of gas and liquid phases may be used for promoting contact between gas and liquid phases in the separation device. In some embodiments, the countercurrent flow may be achieved by introducing the high-pressure vapor phase from the liquid phase oxidation at a lower portion of the separation device, and introducing reflux liquid to at least one and, in some embodiments two or more upper portions.

In some embodiments, the separation zone comprises a single separation device. In other embodiments, the separation zone comprises multiple separation devices, which in some embodiments may be arranged in series. Representative separation devices include but are not limited to distillation columns, distillation towers, dehydration towers, rectifying columns, water-removal columns, high efficiency separation devices, and/or the like, and combinations thereof. In some embodiments, two or more devices may be configured in series with their respective inlets and outlets in fluid communication, such that a high-pressure vapor phase removed from an oxidation reaction vessel flows into the series with separation and apportionment of solvent monocarboxylic acid, water, and by-products in flowing vapor and reverse flows of refluxing liquid in and through the series.

In some embodiments, a liquid of sufficient purity for use as purification solvent may comprise other suitable water sources in addition to the organic-depleted water stream withdrawn from the side draw 345 (e.g., fresh demineralized water and/or other purified sources of water). In some embodiments, the organic-depleted water removed from the separation device via side draw makes up at least about 50% of the solvent for the purification reaction solution and, in some embodiments, between about 80 and about 100%.

Referring again to FIG. 1, liquid effluent comprising solid oxidation products (slurried in the liquid phase reaction mixture is removed from reaction vessel 110 through slurry outlet 114 and directed in stream 115 to crystallization vessel 152, and in turn crystallization vessel 156, for recovery of a solid product (crude aromatic carboxylic acid and oxidation by-products of the feedstock).

In some embodiments, solid crude product may be recovered from the liquid by crystallization in one or more stages, such as in a single crystallization vessel or, as shown in FIG. 1, in a series of multiple stirred crystallization vessels. In some embodiments, the crystallization process comprises sequential reductions in temperature and pressure from earlier to later stages to increase product recovery. By way of example, as shown in FIG. 1, crystallization vessels 152 and 156 may be provided in series and in fluid communication, such that product slurry from vessel 152 may be transferred to vessel 156. Cooling in the crystallization vessels may be accomplished by pressure release. One or more of the crystallization vessels may be vented, as at vents 154 and 158, to remove vapor resulting from pressure let down and generation of steam from the flashed vapor to a heat exchange means (not shown).

Solid product recovered in the crystallization zone may be separated from mother liquor by any suitable technique. Representative techniques include but are not limited to centrifuging, vacuum filtration, pressure filtration, filtration using belt filters, and the like, and combinations thereof. In some embodiments, the resulting solid product may be washed after separation with liquid comprising water, such as pure water or a wash liquid comprising a stream recycled from elsewhere in the process.

As shown in FIG. 1, the crystallization vessel 156 is in fluid communication with a solid-liquid separation device 190. The solid-liquid separation device 190 is configured to receive a slurry of solid product from the crystallization vessel 156. In some embodiments, the solid-liquid separation device 190 is further configured to separate a crude solid product comprising terephthalic acid and by-products from the liquid. In some embodiments, the separation device 190 is a centrifuge, a rotary vacuum filter, a pressure filter, or the like, or a combination thereof. In some embodiments, the separation device 190 comprises a pressure filter configured for solvent exchange (e.g., by positive displacement under pressure of mother liquor in a filter cake with wash liquid comprising water). The oxidation mother liquor resulting from the separation may exit separation device 190 in stream 191 for transfer to mother liquor drum 192. A portion of the mother liquor and, in some embodiments, a major portion of the mother liquor, may be transferred from drum 192 to oxidation reactor 110. In such a way, acetic acid, water, catalyst, and/or oxidation reaction by-products dissolved and/or present as fine solid particles in the mother liquor may be returned to the liquid phase oxidation reaction.

As shown in FIG. 1, the stream 197 may be directed to a purification solution makeup vessel 202. The crude solid product may be slurried in makeup vessel 202 in purification reaction solvent. In some embodiments, as described above, all or at least a portion of the purification reaction solvent comprises an additional liquid phase that comprises an organic-depleted water stream withdrawn from the column 330 at side draw 345. In some embodiments, the purification reaction solvent may be further supplemented with an additional liquid phase (e.g., fresh demineralized water) which, in some embodiments, may be obtained from a holding vessel 204.

In some embodiments, purification in the purification reactor 210 comprises contacting the purification reaction solution (e.g., a liquid comprising water and crude terephthalic acid recovered from the liquid phase oxidation) with hydrogen at elevated temperature and pressure in the presence of a hydrogenation catalyst. In some embodiments, the pressure ranges from about 85 to about 95 kg/cm$^2$. In some embodiments, a portion of the purification liquid reaction mixture may be continuously removed from hydrogenation reactor 210 in stream 211 and directed to a crystallization vessel 220 in a downstream crystallization zone. In crystallization vessel 220, terephthalic acid and reduced levels of impurities may be crystallized from the reaction mixture (e.g., by reducing pressure on the liquid). The resulting slurry of purified terephthalic acid and liquid formed in vessel 220 may be directed to solid-liquid separation device 230 in stream 221. Vapors resulting from pressure letdown in the crystallization reactor 220 may be condensed by passage to heat exchangers (not shown) for cooling. The resulting condensate liquid may be redirected to the process, for example as recycle to purification feed makeup vessel 202, through suitable transfer lines (not shown) and/or be directed to waste water treatment (WWT). Purified terephthalic acid exits solid-liquid separation device 230 in the stream 231. In some embodiments, the purification mother is not used as reflux to the separation device 330, In some embodiments, at least a portion, in some embodiments all or substantially all, of the purification mother liquor may be directed in stream 233 to WWT and/or the like. The solid-liquid separation device 230 may be a centrifuge, a rotary vacuum filter, a pressure filter, or the like, or a combination thereof.

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for manufacturing a purified aromatic carboxylic acid comprising:
   oxidizing a substituted aromatic compound in a reaction zone to form a crude aromatic carboxylic acid;
   transferring a vapor phase from the reaction zone to a separation zone, the vapor phase comprising water and a plurality of organic compounds including oxidation by-products of the substituted aromatic compound;
   removing a high pressure vapor phase from the separation zone, the high pressure vapor phase comprising water and being substantially free of oxidation by-products of the substituted aromatic compound;
   withdrawing an organic-depleted liquid water stream from the separation zone, the organic-depleted liquid water stream being substantially free of oxidation by-products of the substituted aromatic compound;
   combining at least a portion of the organic-depleted liquid water stream with at least a portion of the crude aromatic carboxylic acid in a purification zone; and
   purifying the crude aromatic carboxylic acid in the presence of said at least a portion of the organic-depleted water stream in the purification zone to form a purified aromatic carboxylic acid.

2. The invention of claim 1, wherein the organic-depleted liquid water stream is directed to the purification zone without further treatment to remove organic impurities.

3. The invention of claim 1 wherein the oxidizing comprises contacting the substituted aromatic compound with gaseous oxygen in a liquid phase oxidation reaction mixture comprising a monocarboxylic acid solvent, water, and a catalyst composition.

4. The invention of claim 3 wherein the organic-depleted liquid water stream comprises monocarboxylic acid solvent.

5. The invention of claim 4 wherein the monocarboxylic acid solvent comprises acetic acid.

6. The invention of claim 1 wherein the organic-depleted liquid water stream comprises less than 0.05 wt % alcohol.

7. The invention of claim 1, wherein the organic-depleted liquid water stream comprises less than 0.05 wt % alkyl ester.

8. The invention of claim 1 wherein the separation zone comprises a first dehydration tower and a second dehydration tower coupled to an output of the first dehydration tower.

9. The invention of claim 8 wherein the second dehydration tower comprises a side draw configured for egress of the organic-depleted liquid water stream.

10. The invention of claim 1 wherein the aromatic carboxylic acid is terephthalic acid.

11. The invention of claim 1 wherein the aromatic carboxylic acid comprises terephthalic acid and the oxidation by-products of the substituted aromatic compound comprises paratoluic acid.

12. The invention of claim 11 wherein the organic-depleted liquid water stream comprises less than 1 ppmw of paratoluic acid.

13. The invention of claim 11, wherein the organic-depleted liquid water stream comprises less than 0.05 wt % methanol.

14. The invention of claim 11, wherein the organic-depleted liquid water stream comprises less than 0.05 wt % methyl acetate.

15. The invention of claim 1 wherein the purification zone comprises a hydrogenation reactor.

16. The invention of claim 1 wherein the purifying comprises contacting an aqueous solution that comprises at least a portion of the crude aromatic carboxylic acid and at least a portion of the organic-depleted liquid water stream with hydrogen in the presence of a catalyst.

17. The invention of claim 1, further comprising separating a purification mother liquid from the purified aromatic carboxylic acid.

18. The invention of claim 14, further comprising transferring the purification mother liquor to a waste water treatment facility.

19. The invention of claim 14, wherein the purification mother liquor is not used as reflux to the separation zone.

* * * * *